(12) United States Patent
Kokish et al.

(10) Patent No.: US 7,354,480 B1
(45) Date of Patent: *Apr. 8, 2008

(54) STENT MANDREL FIXTURE AND SYSTEM FOR REDUCING COATING DEFECTS

(75) Inventors: Arkady Kokish, Los Gatos, CA (US); Charles Snyder, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 583 days.

This patent is subject to a terminal disclaimer.

(21) Appl. No.: 10/376,027

(22) Filed: Feb. 26, 2003

(51) Int. Cl.
*B05C 13/02* (2006.01)
*B05C 5/00* (2006.01)
*B05B 13/02* (2006.01)

(52) U.S. Cl. .............. 118/500; 118/320; 118/307; 118/DIG. 11

(58) Field of Classification Search ........... 118/500, 118/502, 319–320, DIG. 11, 300, 305, 307; 427/2.24, 2.25, 2.28, 2.3; 623/1.1, 1.11, 623/1.45, 920, 1.46, 1.47, 1.48; 606/194; 269/48.1, 52; 248/314, 201; 279/2.22, 2.17; 242/130.1, 571, 572; 68/205 R, 206, 205 E; 134/116, 115 R, 147, 153, 184
See application file for complete search history.

(56) References Cited

U.S. PATENT DOCUMENTS

| | | | | |
|---|---|---|---|---|
| 2,801,809 A | * | 8/1957 | Glaner | 242/560 |
| 3,079,099 A | * | 2/1963 | Blain | 242/597.5 |
| 3,796,185 A | * | 3/1974 | Boone | 118/325 |
| 3,980,250 A | * | 9/1976 | Persson | 242/129.5 |
| 3,989,001 A | * | 11/1976 | Brigham et al. | 118/679 |
| 4,629,563 A | | 12/1986 | Wrasidlo | 210/500.34 |
| 4,733,665 A | | 3/1988 | Palmaz | 128/343 |
| 4,800,882 A | | 1/1989 | Gianturco | 128/343 |
| 4,886,062 A | | 12/1989 | Wiktor | 128/343 |
| 4,893,623 A | * | 1/1990 | Rosenbluth | 606/192 |
| 4,906,423 A | | 3/1990 | Frisch | 264/48 |
| 5,037,427 A | | 8/1991 | Harada et al. | 606/108 |
| 5,171,445 A | | 12/1992 | Zepf | 210/500.27 |
| 5,188,734 A | | 2/1993 | Zepf | 210/490 |
| 5,229,045 A | | 7/1993 | Soldani | 264/41 |
| 5,234,457 A | | 8/1993 | Andersen | 606/198 |
| 5,242,399 A | * | 9/1993 | Lau et al. | 604/104 |
| 5,537,729 A | | 7/1996 | Kolobow | 29/527.2 |
| 5,611,775 A | | 3/1997 | Machold et al. | 604/53 |
| 5,624,411 A | | 4/1997 | Tuch | 604/265 |
| 5,628,786 A | | 5/1997 | Banas et al. | 623/1 |
| 5,772,864 A | | 6/1998 | Møller et al. | 205/73 |
| 5,788,626 A | | 8/1998 | Thompson | 600/36 |

(Continued)

FOREIGN PATENT DOCUMENTS

JP 05009726 A * 1/1993

OTHER PUBLICATIONS

English Translated Abstract of JP05009726A.*

(Continued)

*Primary Examiner*—Yewebdar Tadesse
(74) *Attorney, Agent, or Firm*—Squire Sanders & Dempsey LLP

(57) ABSTRACT

A stent mandrel fixture for supporting a stent during the application of a coating substance is provided.

45 Claims, 2 Drawing Sheets

U.S. PATENT DOCUMENTS

| | | | |
|---|---|---|---|
| 5,820,917 A | 10/1998 | Tuch | 427/2.1 |
| 5,823,996 A | 10/1998 | Sparks | 604/96 |
| 5,833,659 A | 11/1998 | Kranys | 604/96 |
| 5,855,598 A | 1/1999 | Pinchuk | 623/1 |
| 5,865,814 A | 2/1999 | Tuch | 604/265 |
| 5,893,568 A * | 4/1999 | Swain et al. | 279/2.22 |
| 5,895,407 A | 4/1999 | Jayaraman | 606/198 |
| 5,897,911 A | 4/1999 | Loeffler | 427/2.25 |
| 5,922,393 A | 7/1999 | Jayaraman | 427/2.3 |
| 5,935,135 A | 8/1999 | Bramfitt et al. | 606/108 |
| 5,948,018 A | 9/1999 | Dereume et al. | 623/1 |
| 6,010,573 A | 1/2000 | Bowlin | 118/620 |
| 6,030,371 A * | 2/2000 | Pursley | 604/527 |
| 6,045,899 A | 4/2000 | Wang et al. | 428/315.7 |
| 6,056,993 A | 5/2000 | Leidner et al. | 427/2.25 |
| 6,120,847 A | 9/2000 | Yang et al. | 427/335 |
| 6,126,686 A | 10/2000 | Badylak et al. | 623/1.24 |
| 6,153,252 A | 11/2000 | Hossainy et al. | 427/2.3 |
| 6,156,373 A | 12/2000 | Zhong et al. | 427/2.28 |
| 6,214,115 B1 | 4/2001 | Taylor et al. | 118/423 |
| 6,245,099 B1 | 6/2001 | Edwin et al. | 623/1.13 |
| 6,258,121 B1 | 7/2001 | Yang et al. | 623/1.46 |
| 6,279,368 B1 | 8/2001 | Escano et al. | 72/342.1 |
| 6,322,847 B1 | 11/2001 | Zhong et al. | 427/2.28 |
| 6,331,191 B1 * | 12/2001 | Chobotov | 623/1.44 |
| 6,364,903 B2 | 4/2002 | Tseng et al. | 623/1.15 |
| 6,387,118 B1 | 5/2002 | Hanson | 623/1.11 |
| 6,395,326 B1 * | 5/2002 | Castro et al. | 427/2.24 |
| 6,517,534 B1 * | 2/2003 | McGovern et al. | 606/41 |
| 6,521,284 B1 | 2/2003 | Parsons et al. | 427/2.24 |
| 6,527,863 B1 * | 3/2003 | Pacetti et al. | 118/500 |
| 6,544,582 B1 * | 4/2003 | Yoe | 427/2.24 |
| 6,565,659 B1 | 5/2003 | Pacetti et al. | 118/500 |

OTHER PUBLICATIONS

U.S. Appl. No. 09/873,020, filed May 31, 2001, Villareal.
U.S. Appl. No. 09/894,242, filed Jun. 27, 2001, Moein.
U.S. Appl. No. 09/894,248, filed Jun. 27, 2001, Pacetti et al.
U.S. Appl. No. 09/896,000, filed Jun. 28, 2001, Pacetti et al.
U.S. Appl. No. 10/254,203, filed Sep. 24, 2002, Kerrigan.
U.S. Appl. No. 10/255,913, filed Sep. 26, 2002, Tang et al.
U.S. Appl. No. 10/304,669, filed Nov. 25, 2002, Madriaga et al.

* cited by examiner

STENT MANDREL FIXTURE AND SYSTEM FOR REDUCING COATING DEFECTS

TECHNICAL FIELD

This invention relates generally to stent mandrel fixtures, and more particularly, but not exclusively, provides a stent mandrel fixture and method for reducing coating defects on stents.

BACKGROUND

Blood vessel occlusions are commonly treated by mechanically enhancing blood flow in the affected vessels, such as by employing a stent. Stents act as scaffoldings, functioning to physically hold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. The struts 12 and the connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

A shortcoming of the above-described method of medicating a stent is the potential for coating defects. While some coating defects can be minimized by adjusting the coating parameters, other defects occur due to the nature of the interface between the stent and the apparatus on which the stent is supported during the coating process. A high degree of surface contact between the stent and the supporting apparatus can provide regions in which the liquid composition can flow, wick, and collect as the composition is applied. As the solvent evaporates, the excess composition hardens to form excess coating at and around the contact points between the stent and the supporting apparatus. Upon the removal of the coated stent from the supporting apparatus, the excess coating may stick to the apparatus, thereby removing some of the coating from the stent and leaving bare areas. Alternatively, the excess coating may stick to the stent, thereby leaving excess coating as clumps or pools on the struts or webbing between the struts.

Accordingly, a new stent mandrel fixture and method are needed to minimize coating defects.

SUMMARY

A stent mandrel fixture for supporting a stent during application of a coating substance to the stent is provided, comprising a mandrel capable of extending through a longitudinal bore of a stent, and a coil member coupled to the mandrel for supporting the stent on the mandrel. The coil member can be sized so as to allow the stent to telescopically shift over the mandrel. The fixture can additionally include a first member connected to one end of the mandrel and a second member connected to the other end of the mandrel. Each of the first and second members can include a sloping side facing one another and the stent.

A system for coating a stent is also provided, comprising a nozzle for depositing a coating substance onto a stent; and a mandrel for supporting and rotating the stent during a coating process. The mandrel comprises a first member for extending through a longitudinal bore of the stent; a second member connected to one end of the first member and including a sloping side facing one end of the stent; and a third member connect to the other end of the first member and including a sloping side facing the other end of the stent, wherein when the sloping side of the second member is facing the nozzle, the sloping side of the third member is facing away from the nozzle and when the sloping side of the second member is facing away from the nozzle, the sloping side of the third member is facing the nozzle. The mandrel can include a spring member circumscribing at least a segment of the first member for supporting the stent and preventing an outer surface of the first member from making contact with an inner surface of the stent.

A method of depositing a coating on a stent is provided, comprising inserting a mandrel having a coil member through a longitudinal bore of a stent, wherein the stent is supported on the coil member; and applying a coating composition to the stent to form a coating.

A method of coating a stent is provided, comprising positioning a stent on a support assembly, the support assembly comprising a first member extending through a longitudinal bore of a stent, a second member coupled to one end of the first member, and a third member coupled to the other end of the first member; applying an atomized coating composition from a nozzle assembly to the stent; and rotating the support assembly to rotate the stent about the longitudinal axis of the stent, wherein during the act of rotating, the atomized coating composition reflects off of the second member to move the stent towards the third member and the atomized coating composition reflects off of the third member to move the stent towards the second member.

A stent mandrel is also provided, comprising a first member having a side; a second member having a side; and a third member having one end in connection with the side of the first member and an opposing end in connection with the side of the second member, wherein the third member extends out from the side of the first or second member at an angle other than 90 degrees.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION

The following description is provided to enable any person having ordinary skill in the art to make and use the invention, and is provided in the context of a particular application and its requirements. Various modifications to the embodiments will be readily apparent to those skilled in the art, and the generic principles defined herein may be applied to other embodiments and applications without departing from the spirit and scope of the invention. Thus, the present invention is not intended to be limited to the embodiments shown, but is to be accorded the widest scope consistent with the principles, features and teachings disclosed herein.

Figure 1:
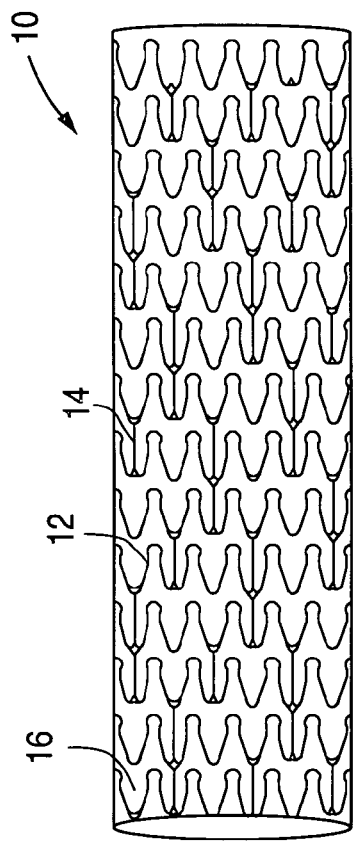
FIG. 1 illustrates a conventional stent.
Figure 2:
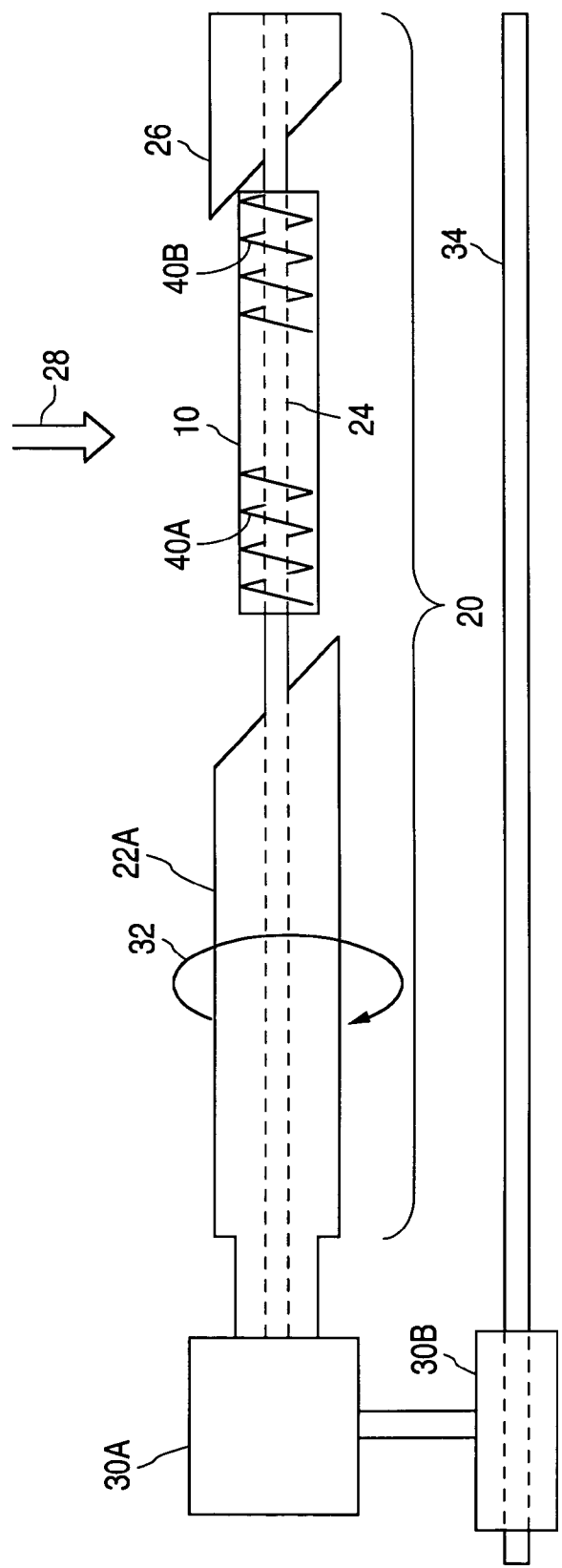
FIG. 2 illustrates a stent mandrel fixture in accordance with an embodiment of the invention.

FIG. 2 illustrates a stent mandrel fixture 20 in accordance with an embodiment of the invention. The fixture 20 for supporting the stent 10 is illustrated to include a support member 22A, a mandrel 24, a wire, coil or springs 40A and 40B, and a lock member 26. The support member 22A can connect to a motor 30A so as to provide rotational motion about the longitudinal axis of the stent 10, as depicted by arrow 32, during a coating process. Another motor 30B can also be provided for moving the mandrel fixture 20 in a linear direction, back and forth, along a rail 34.

The wires 40A and 40B extend from the mandrel 24 and circumscribe the mandrel 24 and support the stent 10 during a coating process. The wires 40A and 40B can be short springs of 2-5 coils each and made from about 0.006 to about 0.008 inch diameter wire. The diameter of the wire varies based on the stent 10 characteristics. In one embodiment, the outer diameter of the springs 40A and 40B can be less than the inner diameter of the stent 10 (as mounted on the coils 40A and 40B) for allowing the stent 10 to move telescopically back and forth between support member 22A and lock member 26, as will be described below. With smaller diameter coils 40A and 40B, the angular speed of the stent 10 as compared to the coils 40A and 40B is obviously different. The combination of linear as well as rotational movement of the stent 10 relative to the coils 40A and 40B reduces or eliminates the gathering of coating composition between the two components. The springs 40A and 40B can be made from or coated with a non-stick material such as TEFLON. It will be appreciated by one of ordinary skill in the art that additional or fewer springs can be used. It should be also noted, however, that the use of springs 40A and 40B is not required. In one alternative embodiment, the mandrel 24 can have a duel diameter, such that the stent 10 rests on the segment of the mandrel 24 having the bigger diameter. In yet another embodiment of the invention, the stent 10 can be securely pinched between support member 22A and lock member 26 during the coating process.

Figure 3:
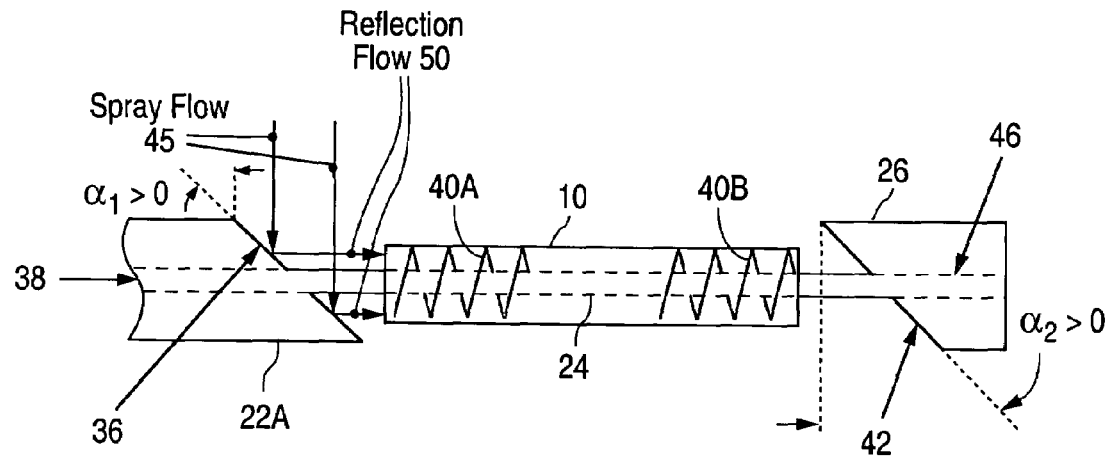
FIG. 3 illustrates another view of stent mandrel fixture of FIG. 2.

Referring to FIG. 3, support member 22A includes a sloping side or end portion 36, tapering at an angle $\alpha_1$ of about 15° to about 75°, more narrowly from about 30° to about 60°. By way of example, the angle $\alpha_1$ can be about 45°. In accordance with one embodiment of the invention, the mandrel 24 can be permanently affixed to the sloping end portion 36. Alternatively, the support member 22A can include a bore 38 for receiving a first end of the mandrel 24. The first end of mandrel 24 can be threaded to screw into the bore 38 or, alternatively, can be retained within the bore 38 by a friction fit. The bore 38 should be deep enough so as to allow the mandrel 24 to securely mate with the support member 22A. The depth of the bore 38 can also be overextended so as to allow a significant length of the mandrel 24 to penetrate or screw into the bore 38. This would allow the length of mandrel 24 to be adjusted to accommodate stents of various sizes.

The outer diameter of the mandrel 24 is smaller than the inner diameter of the stent 10 so as to prevent the outer surface of the mandrel 24 from making contact with the inner surface of the stent 10. A sufficient clearance between the outer surface of the mandrel 24 and the inner surface of the stent 10 should be provided to prevent the mandrel 24 from obstructing the pattern of the stent 10 body during the coating process. If the stent 10 is not securely pinched between the support member 22A and the lock member 26, the required clearance can be provided by the springs 40A and 40B, which can support the stent 10 without obstructing the pattern of the stent 10 body during the coating process. By way of example, the outer diameter of mandrel 24 can be from about 0.010 inches (0.254 mm) to about 0.021 inches (0.533 mm) when the stent 10 has an inner diameter of between about 0.025 inches (0.635 mm) and about 0.035 inches (0.889 mm). In addition, the length of the mandrel 24 is longer than that of stent 10 to be coated.

The lock member 26 includes a sloping side or end portion 42 having a tapered angle $\alpha_2$. The angle $\alpha_2$ can be the same as or different from the angle $\alpha_1$. A second end of the mandrel 24 can be permanently affixed to the lock member 26 if the first end is disengagable from the support member 22A. Alternatively, in accordance with another embodiment, the mandrel 24 can have a threaded second end for screwing into a bore 46 of the lock member 26. The bore 46 can be of any suitable depth that would allow the lock member 26 to be incrementally moved closer to the support member 22A. In accordance with yet another embodiment, a non-threaded second end of the mandrel 24 and the bore 46 combination can be employed such that the second end can be press-fitted or friction-fitted within the bore 46.

During a coating process, a spray flow 45, discharged from a nozzle assembly 28, comprising a coating composition (and atomizing air, if the composition is atomized), deflects off of the surface of the sloping end 36 of the support member 22A to become a reflection flow 50. The sloping end 36 receives and deflects the composition when the surface of the sloping end 36 is facing the nozzle assembly 28 or the direction from which the spray flow 45 is discharged. When sloping end 36 is facing the nozzle assembly 28, the sloping end 42 of the locking member 26 is facing away from the nozzle assembly 28 so as not to interfere with the movement of the stent 10 by deflecting the coating composition at the stent. This reflection flow 50 pushes the stent 10 in an axial direction away from the support member 22A. When engine 30A rotates the fixture 20 and the stent 10 (optionally in combination with the engine 30B moving the locking member 26) so as to place the locking member 26 in position to intersect the spray flow 45 on the surface of the sloping end 42, the spray flow 45 bounces off of the surface of the sloping end 42 to push the stent 10 back towards the support member 22A. Accordingly, the stent 10 can be displaced back and forth between the support member 22A and the locking member 26 during the rotation of the fixture 20. As a result, the contact between the support device and the stent 10 is not a fixed region such that damage to a coating film deposited on the stent is reduced or eliminated.

The components of the coating substance or composition can include a solvent or a solvent system comprising multiple solvents, a polymer or a combination of polymers, a therapeutic substance or a drug or a combination of drugs. The composition can be used to coat stents or other implantable medical devices. Representative examples of polymers that can be used to coat a stent or medical device include ethylene vinyl alcohol copolymer (commonly known by the generic name EVOH or by the trade name EVAL); poly (hydroxyvalerate); poly(L-lactic acid); polycaprolactone; poly(lactide-co-glycolide); poly(glycerol-sebacate); poly (hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly (trimethylene carbonate); poly(iminocarbonate); copoly (ether esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and mixtures and combinations thereof.

The therapeutic substance or drug can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, dexamethasone, and rapamycin.

Figure 4:
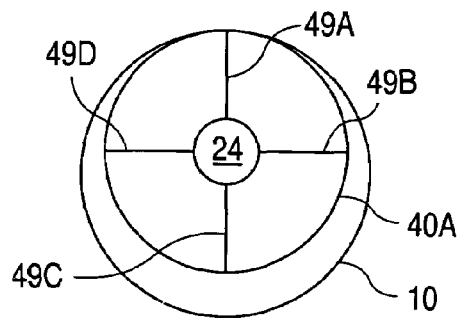
FIG. 4 illustrates a cross section a portion of the stent mandrel fixture of FIG. 2.

FIG. 4 illustrates a cross section a portion of the stent mandrel fixture 20 of FIG. 2. Shown in FIG. 4 is the mandrel 24 circumscribed (at least on revolution) by the coil 40A. The spring 40A has an outer diameter greater than an outer diameter of the mandrel 24 but less than the inner diameter of the stent 10. The spring 40A can include a plurality of support structures, e.g., 49A, 49B, 49C, and 49D that extend inwards from the spring 40A to contact the mandrel 24. The support structures 49A-49D support the spring 40A so that the coils of the spring 40A support the stent 10 without the stent 10 coming into contact with the surface of the mandrel 24. It will be appreciated by one of ordinary skill in the art that fewer (i.e., 3) or additional support structures can be used. It will be further appreciated that the spring 40B can be substantially similar to the spring 40A.

Figure 5:
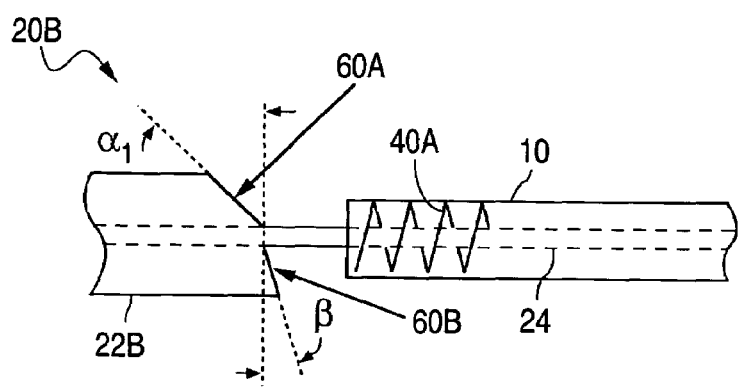
FIG. 5 illustrates a stent mandrel fixture in accordance with another embodiment of the invention.

FIG. 5 illustrates a stent mandrel fixture 20B in accordance with another embodiment of the invention. The stent mandrel fixture includes a support member 22B, mandrel 24 and a locking member (not shown) that can be substantially similar to the locking member 26. The support member 22B is substantially similar to the support member 22A except that the sloping side of the support member 22B comprises two separate walls or surfaces 60A and 60B. The sloping surface 60A can have an angle $\alpha_1$ (i.e., the same as the angle $\alpha_1$ of the sloping end 36) and the sloping surface 60B can have an angle of $\beta$, wherein $\beta$ is less than $\alpha_1$ (i.e., steeper). During a spray coating process, when the sloping surface 60A is facing the spray flow (due to rotation) of a nozzle, the surface 60A deflects the spray flow and atomized air against the stent 10, thereby pushing the stent 10 in an axial direction away from the surface 60A. When the support member 22B has rotated 180° the sloping surface 60B minimizes shadowing of the stent 10 from the spray flow, thereby ensuring an even coating on the stent 10. It will be appreciated by one of ordinary skill in the art that the locking member of the stent mandrel fixture 20B can have a sloping end substantially similar to the sloping end of the support member 22B.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent mandrel fixture for supporting a stent during formation of a coating substance, comprising:
   a mandrel capable of extending through a longitudinal bore of a stent;
   a first member connected to one end of the mandrel;
   a second member connected to the other end of the mandrel; and
   a coil member coupled to the mandrel for supporting the stent on the mandrel and to prevent the stent from contacting an outer surface of the mandrel during formation of the coating, wherein the first and second members include a sloping side facing one another and the stent.

2. The fixture of claim 1, wherein the stent is configured to move between the first member and the second member during formation of the coating.

3. The fixture of claim 1, wherein the stent is configured to move relative to the mandrel or the coil member.

4. The fixture of claim 1, wherein the fixture is adapted to move the stent rotationally and/or linearly.

5. A stent mandrel fixture for supporting a stent during formation of a coating substance, comprising:
   a mandrel capable of extending through a longitudinal bore of a stent;
   a first member connected to one end of the mandrel;
   a second member connected to the other end of the mandrel; and
   a coil member coupled to the mandrel for supporting the stent on the mandrel and to prevent the stent from contacting an outer surface of the mandrel during formation of the coating, wherein the first and second members include a side facing the stent, wherein each of the sides includes a first sloping segment and a second sloping segment having a different degree of sloping than the first sloping segment.

6. The fixture of claim 5, wherein the stent is configured to move between the first member and the second member during formation of the coating.

7. The fixture of claim 5, wherein the stent is configured to move relative to the mandrel or the coil member.

8. The fixture of claim 5, wherein the fixture is adapted to move the stent rotationally and/or linearly.

9. A system for coating a stent, comprising:
   a nozzle for depositing a coating substance onto a stent; and
   a mandrel for supporting and rotating the stent during a coating process, the mandrel comprising
      a first member for extending through a longitudinal bore of the stent;
      a second member connected to one end of the first member and including a sloping side facing one end of the stent;
      a third member connected to the other end of the first member and including a sloping side facing the other end of the stent, wherein when a surface of the sloping side of the second member is facing the nozzle, a surface of the sloping side of the third member is facing away from the nozzle, and when the surface of the sloping side of the second member is facing away from the nozzle, the surface of the sloping side of the third member is facing the nozzle; and
      a spring member circumscribing at least a segment of the first member for supporting the stent and preventing an outer surface of the first member from making contact with an inner surface of the stent.

10. The system of claim 9, wherein the stent is capable of moving telescopically on the spring member over the first member.

11. The system of claim 9, wherein the sloping sides include a first segment having a first sloping angle and a second segment having a second sloping angle different than the first sloping angle.

12. The fixture of claim 9, wherein the stent is capable of moving relative to the first member.

13. The fixture of claim 9, wherein the stent is capable of moving between the second member and the third member.

14. The fixture of claim 9, wherein the fixture is adapted to rotate the stent and/or move the stent in a linear direction.

15. A stent fixture for supporting a stent during formation of a coating substance, comprising:
   a first member capable of extending at least partially through a longitudinal bore of a stent; and
   a second member extending in a spiral formation around the first member to make contact with an inner side of the stent, to support the stent on the first member and to prevent the inner side of the stent from contacting an outer surface of the first member during formation of the coating.

16. The fixture of claim 15, wherein the second member is a wire.

17. The fixture of claim 15, wherein the second member is a spring.

18. The fixture of claim 15, wherein the second member is coil.

19. The fixture of claim 15, wherein the second member is made from a non-stick material.

20. The fixture of claim 15, wherein the second member is coated with a non-stick material.

21. The fixture of claim 15, wherein the first member is longer than the stent.

22. The fixture of claim 15, wherein the stent is capable of moving back and forth on the second member.

23. The fixture of claim 15, additionally including a third member coupled to one end of the first member and a fourth member coupled to an opposing end of the first member, the third and forth members preventing the stent from sliding off of the second member.

24. The fixture of claim 15, wherein at least one part of the fixture is capable of rotating during formation of the coating.

25. The fixture of claim 15, wherein the coating substance includes one or a combination of a polymer, a solvent, and a drug.

26. The fixture of claim 15, wherein the fixture is used during a spray application process.

27. The fixture of claim 15, wherein the fixture is capable of moving the stent linearly.

28. A stent fixture for supporting a stent during formation of a coating substance, comprising:
- a first member capable of extending at least partially through a longitudinal bore of a stent;
- a second member extending in a spiral formation around the first member to make contact with an inner side of the stent, to support the stent on the first member and to prevent the inner side of the stent from contacting an outer surface of the first member during formation of the coating; and
- elements for supporting the second member on the first member.

29. The fixture of claim 28, wherein the fixture is capable of moving the stent in a rotational and/or linear direction.

30. The fixture of claim 28, wherein the stent is capable of moving relative to the second member.

31. A stent support fixture for supporting a stent during formation of a coating substance, comprising:
- a first member for extending through a longitudinal bore of the stent such that the first member does not contact the stent;
- a second member connected to one end of the first member and including a sloping side facing one end of the stent, wherein the sloping side is at least large enough so that the second member is not capable of penetrating into the one end of the stent; and
- a third member connected to the other end of the first member and including a sloping side facing the other end of the stent, wherein the sloping side is at least large enough so that the third member is not capable of penetrating into the other end of the stent.

32. The stent support fixture of claim 31, wherein the second member does not extend over the stent if the stent is in contact with the second member.

33. The stent support fixture of claim 31, wherein the second member does not extend over the stent if the stent is in contact with the second member and wherein the third member does not extend over the stent if the stent is in contact with the third member.

34. The stent support fixture of claim 31, wherein the sloping side of the second and/or third member includes a first sloping segment and a second sloping segment having a different degree of sloping than the first sloping segment.

35. The stent support fixture of claim 31, wherein the second member can be moved towards or away from the third member.

36. The stent support fixture of claim 31, wherein the second and/or third member is adjustably connected to the first member.

37. The stent support fixture of claim 31, wherein the first member is longer than the stent.

38. The stent support fixture of claim 31, additionally including a fourth member for preventing the outer surface of the first member from contacting an inner side of the stent.

39. The stent support fixture of claim 38, wherein the fourth member is a coil, spring or a wire.

40. The stent support fixture of claim 31, wherein the fixture can be rotated during the formation of the coating.

41. The fixture of claim 31, wherein the fixture is used during a spray application process.

42. The fixture of claim 31, wherein the fixture is capable of rotating the stent and/or moving the stent in a linear direction.

43. The fixture of claim 31, wherein the stent is configured to move relative to the first member.

44. The fixture of claim 31, wherein the stent is configured to move between the second member and the third member.

45. The fixture of claim 31, wherein the stent is configured to move relative to the second member.

* * * * *